United States Patent [19]

Durkan

[11] Patent Number: 4,457,303
[45] Date of Patent: Jul. 3, 1984

[54] RESPIRATING GAS SUPPLY CONTROL METHOD AND APPARATUS THEREFOR

[75] Inventor: Gerald Durkan, Altoona, Pa.

[73] Assignee: Tritec Industries, Inc., Wethersfield, Conn.

[21] Appl. No.: 210,654

[22] Filed: Nov. 26, 1980

[51] Int. Cl.³ .............................................. A61M 16/00
[52] U.S. Cl. .......................... 128/204.24; 128/204.26; 128/207.18; 128/205.23
[58] Field of Search ...................... 128/204.21, 204.22, 128/204.23, 204.24, 204.18, 204.19, 204.25, 204.26, 205.18, 205.24, 204.29, 207.18, 201.27, 201.28, 202.22, 205.23

[56] References Cited

U.S. PATENT DOCUMENTS

| | | | |
|---|---|---|---|
| 3,333,584 | 8/1967 | Andreasen et al. | 128/202.22 |
| 3,357,428 | 12/1967 | Carlson | 128/145.8 |
| 3,659,598 | 5/1972 | Peters et al. | 128/145.8 |
| 3,736,949 | 5/1973 | Wolter et al. | 137/102 |
| 3,834,382 | 9/1974 | Lederman et al. | 128/145.8 |
| 3,889,669 | 5/1975 | Weigl | 128/145.8 |
| 3,910,270 | 10/1975 | Stewart | 128/145.8 |
| 3,952,740 | 4/1976 | Scurlock | 128/145.8 |
| 4,054,133 | 10/1977 | Myers | 128/142.2 |
| 4,057,059 | 11/1977 | Reid, Jr. et al. | 128/145.8 |
| 4,106,503 | 8/1978 | Rosenthal et al. | 128/200.18 |
| 4,120,300 | 10/1978 | Tiep | 128/203 |
| 4,141,354 | 2/1978 | Ismach | 128/145.6 |
| 4,206,754 | 6/1980 | Cox et al. | 128/204.21 |
| 4,281,651 | 8/1981 | Cox | 128/205.23 |
| 4,316,182 | 2/1982 | Hodgson | 128/204.21 |
| 4,323,064 | 4/1982 | Hoenig | 128/204.21 |
| 4,381,774 | 5/1983 | Schreiber et al. | 128/202.22 |

OTHER PUBLICATIONS

Mon, U.S. Army Electronics Research and Development Command, Harry Diamond Laboratories, "The Design of a Fluidic Oxygen Intermittent-Demand Flow Device", HDL-TM-80-14, Mar. 1980.
ASME Publication 78-WA-DSC-3, George Mon, "Basic Design Concepts of Laminar Digital Logic Elements Using Proportional Amplifiers with Feedback", D. Auerbach et al., Chest, 74:1, Jul. 1978, pp. 39-44.

*Primary Examiner*—Henry J. Recla
*Attorney, Agent, or Firm*—Griffin, Branigan & Butler

[57] ABSTRACT

A fluidically-operated respirator comprises an apneic event circuit (10) and a demand gas circuit (20). The apneic event circuit (10) comprises a variable capacitance device (132) and an exhaust means (130) which rapidly discharge fluid from the circuit (10) when an inspiration occurs. If an apneic event occurs, the circuit (10) activates one or more signals (136) as a predetermined volume of fluid is built up in the circuit (10). The demand gas circuit (20) of the respirator supplies respirating gas to a patient at the beginning of an inspiration and for a time period which is a fraction of the duration of the inspiration.

8 Claims, 9 Drawing Figures put port of the first generating means is connected to a fluidically-operated apneic event circuit which includes a variable volume capacitance device (such as an elastomeric balloon) operating in conjunction with an exhaust valve. The apneic event circuit selectively activates one or more signaling means (such as a counter, an alarm, or an ECG monitor) when a patient has not inspired within a predetermined time.

A second output port of the first generating means is connected to a fluidically-operated demand gas controller circuit. In its various embodiments the demand gas controller circuit includes second generating means responsive to the first fluid signal for generating a second fluid signal having a duration related to the duration of the first fluid signal by a pre-determined relationship. The demand oxygen controller circuit further includes source means including valve means responsive to the second fluid signal for controlling the application of a respirating gas to a patient for a time period relative to the duration of the second fluid signal. Preferably the duration of application of the respirating gas to the patient is less than 0.25 of the duration of an inspiration.

Laminar proportional amplifiers are used as sensing means to sense very small pressures, such as those created by initial attempts to inspire and expire.

BRIEF DESCRIPTION OF THE DRAWINGS

The foregoing and other objects, features, and advantages of the invention will be apparent from the following more particular description of preferred embodiments as illustrated in the accompanying drawings in which reference characters refer to the same parts throughout the various views. The drawings are not necessarily to scale, emphasis instead being placed upon illustrating the principles of the invention.

DETAILED DESCRIPTION OF THE DRAWINGS

Figure 1:
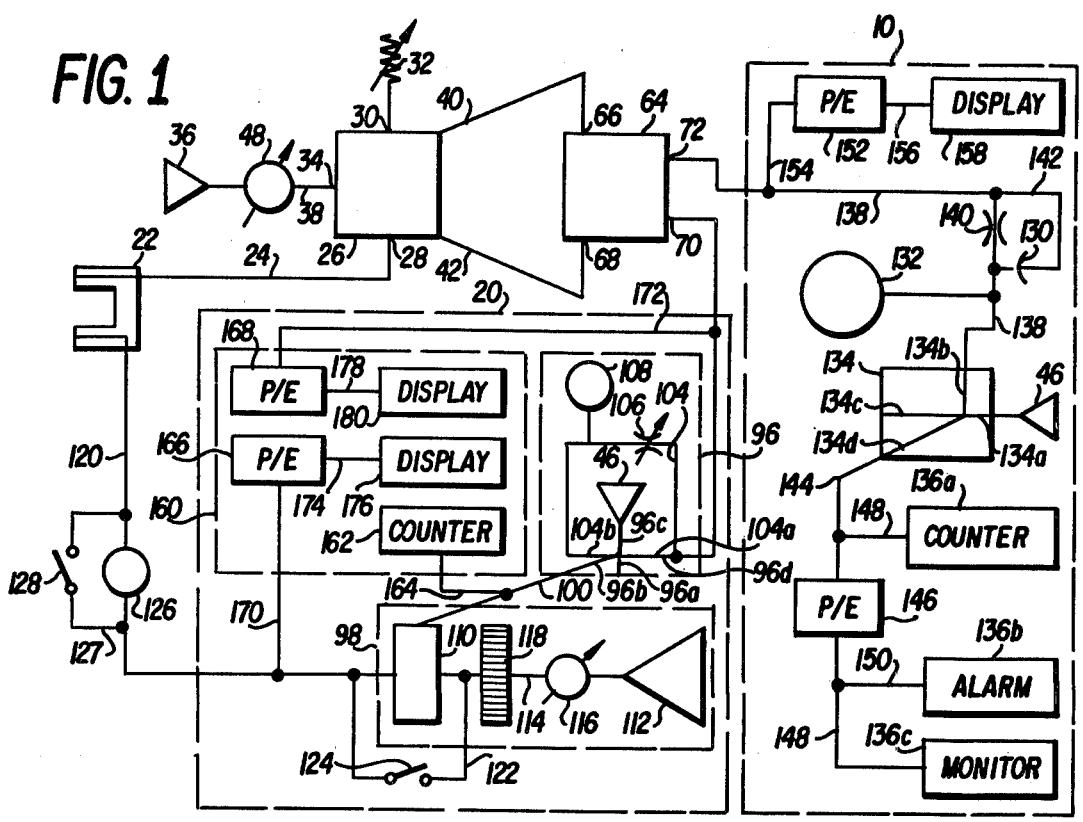
FIG. 1 is a schematic diagram of a respirator apparatus according to one embodiment of the invention.

FIG. 1 illustrates a respirator apparatus according to one embodiment of the invention which includes an apneic event circuit 10 and a demand gas controller circuit 20. The embodiment of FIG. 1 further includes a nasal cannula, or nasal prongs 22, connected by a sensing line 24 to a sensing means 26. When there is a nasal blockage, such as by polyps, for instance, a mask can be used instead of nasal prongs 22. For purpose of brevity, any fluid conveying means, such as a duct, pipe, channel, or other closed fluid conduit is hereinafter referred to as a line.

Sensing means 26 is a device capable of sensing the direction and duration of pressure flow in a patient's respiratory system. That is, sensing means 26 is capable of detecting negative pressure created by a patient's attempt to inspire and positive pressure created by an expiration. As generally shown in FIG. 1, sensing means 26 includes a first control port 28 connected to sensing line 24; a second control port 30 fluidically connected to bias control valve 32; a power stream port 34 connected by a line 38 to a fluid source 36; and, two output ports, or output legs, 40 and 42.

The fluid source 36 shown connected to sensing means 26 in FIG. 1 may be a small pump or conventional wall supply device for providing air, oxygen, or other desired fluid to the respirator apparatus. While the embodiments hereinafter described employ fluidic elements connected to one of a plurality of fluid sources 46 (each source 46 basically resembling fluid source 36), it should be understood that the fluidic elements may be instead connected by suitable connectors to a single source, such as source 36. When desired, a restrictive device 48, such as a variable restrictor or a pressure regulator, may be connected intermediate any source and a fluidic element.

Figure 2:
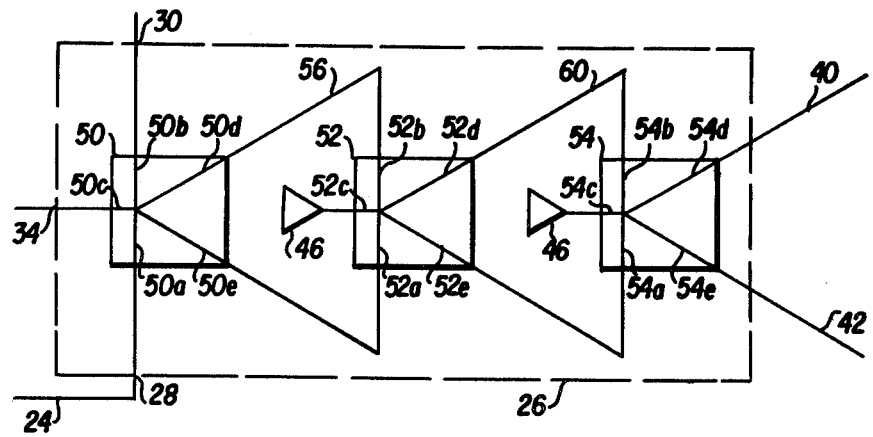
FIG. 2 is a schematic diagram illustrating a sensing means suitable for use in the invention.

As seen in FIG. 2, one embodiment of sensing means 26 suitably comprises a plurality of fluid amplifier devices. In particular, the embodiment of FIG. 2 includes a three stage amplifier network comprising fluid amplifiers 50, 52, and 54. It should be understood, however, that other embodiments of sensing means 26 may have any suitable number of stages depending on the degree of amplification desired. The fluid amplifiers each have first control ports (denoted as 50a, 52a, and 54a, respectively); second control ports (50b, 52b, 54b, respectively); power stream ports (50c, 52c, 54c, respectively); first output ports (50d, 52d, 54d, respectively); and, second output ports (50e, 52e, 54e, respectively).

The amplifiers 50, 52, and 54 are connected in a three stage configuration in the following manner: output port 50d is connected to control port 52b by line 56; output port 50e is connected to control port 52a by line 58; output port 52d is connected to control port 54c by a line 60; and, output port 52e is connected to control port 54a by a line 62. Each power stream input port is connected to a fluid source: port 52c and 54c are connected to the source 46 while port 50c is connected to the source 36 via line 34. As seen in FIG. 2, control port 50a is connected to the sensing line 24; control port 50b is essentially the second control port 30 of sensing means 26; output port 54d is connected to output leg 40 of sensing means 26; and, output port 54e is connected to output leg 42 of sensing means 26.

The amplifiers 50, 52, and 54 of the FIG. 2 embodiment of sensing means 26 are connected so that there is a 6:1 gain in each stage of amplification. The amplifiers 50, 52, and 54 of FIG. 2 may either be conventional fluid flow fluidic amplifiers operated at a sufficiently low pressure that the flow becomes laminar or laminar flow fluidic amplifiers. Laminar flow fluidic amplifiers are highly sensitive and use laminar flow rather than turbulent flow as in typical Coanda type devices. The laminar flow fluidic amplifiers of this type are available through Tritec, Inc. of Columbia, Md. In either case, the sensing means 26 is generally capable of sensing a first instance of inspiration with a negative pressure of approximately 0.5 millimeters of water.

The respirator apparatus of FIG. 1 further comprises first generating means 64 which includes a first control port 66, a second control port 68, a first output port or leg 70, and a second output port or leg 72.

Figure 3A:
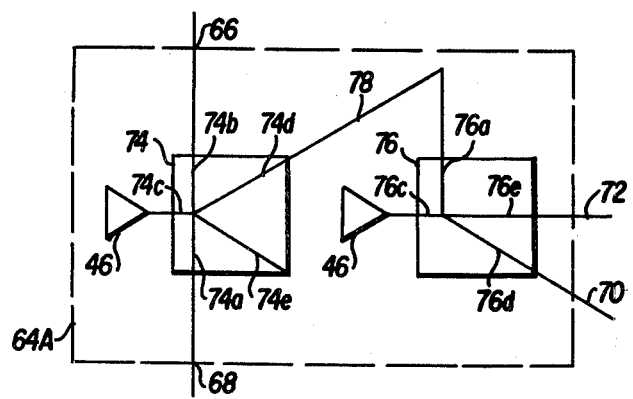
FIGS. 3A, 3B, and 3C are schematic diagrams illustrating differing alternate embodiments of first generating means suitable for use in the invention.

FIG. 3A illustrates in more detail an embodiment of generating means suitable for use with the invention. Generating means 64A of FIG. 3A comprises a fluidic

RESPIRATING GAS SUPPLY CONTROL METHOD AND APPARATUS THEREFOR

BACKGROUND

This invention pertains to respirator apparatus and methods for operating the same, and particularly to such apparatus and operating methods which feature intermittent demand oxygen flow and/or apneic event detection.

Intermittent demand oxygen flow has been tried in the past as an attempt to reduce high costs generally involved in supplying oxygen flow to a patient. D. Auerbach et al. (Chest, 74: July 1, 1978, pp. 39–44) briefly review the history of such attempts and report test results observed with an oxygen cannula system using intermittent-demand nasal flow. The device reported by Auerbach et al. uses a spring-loaded diaphragm in conjunction with a cannula to sense, in two distinct modes, either the negative pressure created by inspiration or the positive pressure created by expiration. In a negative mode the reported device supplies oxygen to the patient as long as negative pressure is detected; in the positive mode oxygen is supplied as long as a positive pressure is not detected.

Fluidic logic elements have also been used in intermittent demand oxygen systems to sense negative and positive pressures created by inspiration and expiration. In this regard, U.S. Pat. No. 3,976,065 to Durkan discusses prior art ventilators employing fluidic elements and further discloses a digital fluidic ventilator wherein a single fluidic flip-flop serves as a primary control element and wherein any one of a plurality of operating modes is obtained by adjusting a bias signal applied to the flip-flop.

Prior art intermittent demand oxygen devices, whether sensing negative or positive pressure, supply oxygen to a patient substantially throughout the duration of an inspiration. If a given patient were to breathe at the rate of 10 breaths per minute, for example, each breath would average 6 seconds. For such a patient, an inspiration would normally be sensed for about 2 seconds of the 6 seconds per breath; an expiration would normally be sensed for the four remaining seconds. Prior art devices, therefore, would supply oxygen for the full duration of inspiration—in this case, 2 seconds.

In some existing devices, such as that tested by Auerbach et al., supra, the oxygen supplied for the full duration of inspiration tends to commence with a surge in the pattern of flow. Heretofore this surge has been considered unnecessary and wasteful. In some devices other fluidic elements, such as a flowmeter, for example, have been incorporated intermediate the patient and the oxygen supply to dampen the surge.

The applicant has clinically observed, however, that in the breathing process oxygen is absorbed into the blood essentially only during an early stage of inspiration. That is, it is during an early stage of inspiration that oxygen effectively reaches the alveoli. Oxygen applied during the latter stages of inspiration remains in "dead spaces" such as the pharynx, trachea, and bronchial tubes. Hence, the applicant has observed and concluded that in operating respirator apparatus it is more advantageous to apply a greater volume of oxygen per second and to apply the oxygen only during an effective early stage of inspiration rather than to apply a conventional volume per second throughout the duration of inspiration.

For the case described above, the effective early stage may last for approximately 0.25 seconds. For most cases, the effective early stage is less than approximately one-quarter and usually approximately one-eighth of the duration of the inspiration. Therefore, if oxygen were supplied at twice the normal volume per second rate (for example: 100 cc/sec. rather than 50 cc/sec.), a savings of more than one-half—and in most instances more than three-quarters—would be realized. Present day intermittent demand oxygen devices are not capable of operating in accordance with this effective early stage inspiratory phenomenon.

Various prior art respirator apparatus attempt to detect apneic events. Basically, apnea is a breathing disorder that may be caused by cessation of central nervous system output, by upper airway obstruction, or by a combination of the two. This disorder has been implicated in the Sudden Infant Death Syndrome. The condition is also especially hazardous in patients with chronic obstructive lung disease since dangerous cardiac arrhythmias can occur due to the anoxia.

Of the prior art devices the attempt to detect apneic events, many (including the devices disclosed in U.S. Pat. No. 3,357,428 to Carlson and 4,206,754 to Cox) periodically generate electrical (as opposed to fluidic) signals which are electrically monitored to determine when a patient has ceased to breathe satisfactorily and which activate an alarm as a warning indicator.

Prior art respirators which utilize fluidic signals to detect apneic events basically employ fixed capacitance reservoirs for either gauging or controlling the length of time between inspirations. Examples of such respirators are seen in U.S. Pat. Nos. 3,910,270 to Stewart; 3,659,598 to Peters et al.; and, 4,141,354 to Ismach. In apneic event detectors using fluidic signals, however, fixed volume capacitances are inadequate since fluid compression in a fixed volume is not compatible with the low pressures often used in a fluidic logic circuit. Moreover, the prior art fixed volume capacitances exhaust through fluidic logic devices themselves and at a rate much slower than what is desirable in an efficient apneic detector.

In view of the above, an object of this invention is to provide a respirator apparatus and method of operating the same wherein respirating gas is supplied to a patient substantially at the beginning of an inspiration and for a time period thereafter which is a fraction of the duration of inspiration.

An advantage of this invention is the provision of an economical and efficient respirator apparatus allowing the conservation of a respirating gas, such as oxygen.

Another object of this invention is to provide a respirator apparatus having an fluidically-operated apneic event detector.

A further advantage of this invention is the provision of a respirator apparatus having an apneic event detector with a variable volume capacitance compatible with fluidic logic elements and means for rapid exhaust thereof.

SUMMARY

A respirator apparatus includes means for sensing either an inspiration or an expiration of a patient and first generating means for generating at either a first or a second output port a first fluid signal indicative of the duration of the inspiration or expiration. The first out-amplifier 74 and a NOR gate 76. The amplifier 74 comprises a first control port 74a; a second control port 74b; a power stream port 74c; a first output port 74d; and, a second output 74e. In the FIG. 3A embodiment control ports 74a and 74b are essentially control ports 68 and 66, respectively, of first generating means 64A; power stream port 74c is connected to the source 46; and, output port 74e is vented to atmosphere. NOR gate 76 comprises a control port 76a; a power stream port 76c; a first output port 76d; and, a second output port 76e. From FIG. 3 it should be understood that power stream 76c is connected to the source 46 and that output ports 76d and 76e are connected to the output legs 70 and 72, respectively, of first generating means 64. NOR gate 76 is connected to amplifier 74 by a line 78 which connects output port 74d to control port 76a.

Figure 3B:
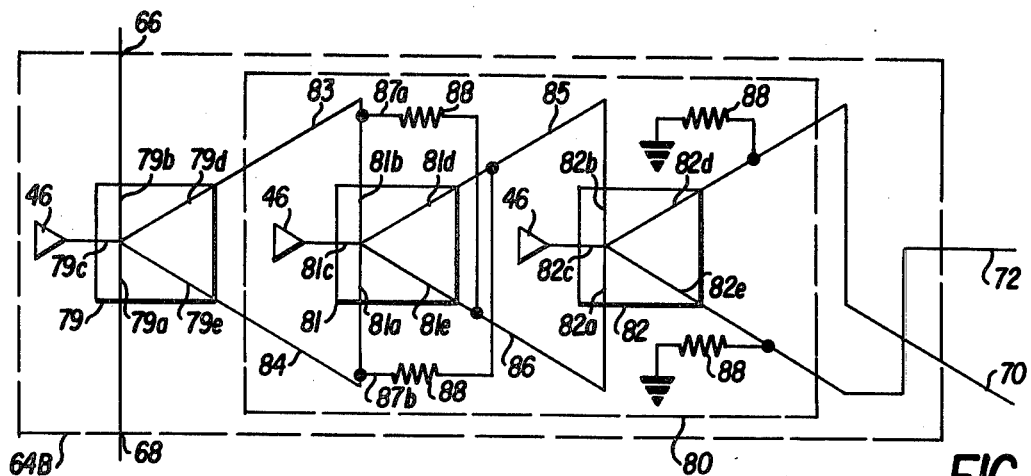

FIG. 3B illustrates a second embodiment of a first generating means suitable for use with the invention. In particular, FIG. 3B illustrates a first generating means 64B which comprises a laminar proportional fluidic amplifier 79 and a fluidic laminar proportional flip-flop 80. The fluidic flip-flop 80 further comprises two laminar proportional amplifiers 81 and 82. Each of the amplifiers 79, 81, and 82 have input ports, power stream ports, and output ports labeled in the alphabetical convention established by the amplifiers 50, 52, 54, and 74 discussed above. Likewise, each amplifier has its power stream input connected to the sources 46.

Amplifier 81 of flip-flop 80 is connected to the amplifier 79 by lines 83 and 84—Line 83 connects control port 81b to output port 79d and line 84 connects control port 81a to output port 79e. The amplifiers 81 and 82 of flip-flop 80 are interconnected by lines 85 and 86 and by two feedback paths hereinafter described. Line 85 connects output port 81d to control port 82b and line 86 connects output port 81e to control port 82a. Feedback path 87a interconnects output port 81e and input port 81b of amplifier 81 and feedback path 87b interconnects output port 81d and input port 81a of amplifier 81. Control input ports 79a and 79b are essentially control ports 68 and 66, respectively, of first generating means 64B and output ports 82d and 82e connect to output legs 70 and 72, respectively. Various resistances, generally denoted as 88, are positioned at various points in the flip-flop 80, including on the feedback paths 87a and 87b.

Figure 3C:
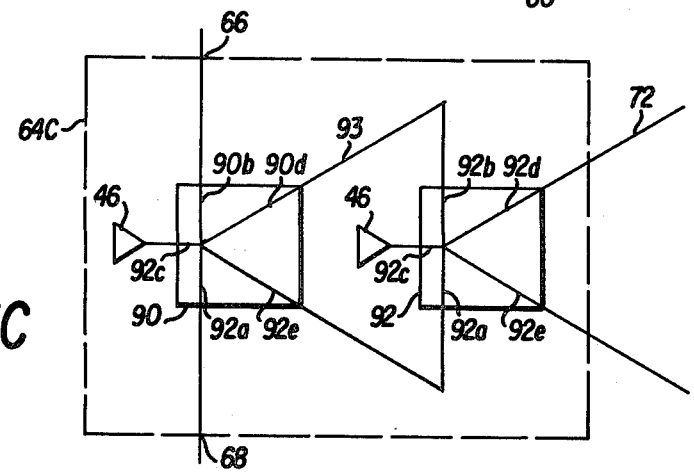

FIG. 3C illustrates a third embodiment of a first generating means also suitable for use with the invention. In particular, FIG. 3C illustrates a first generating means 64C which comprises a proportional fluidic amplifier 90 and a bistable fluidic flip-flop 92. Amplifier 90 and flip-flop 92 have input ports, power stream ports, and output ports labeled in the alphabetical convention mentioned above. Flip-flop 92 is connected to the amplifier 90 by lines 93 and 94—line 93 connects control port 92b to output port 90d and line 94 connects control port 92a to output port 90c. Control ports 90a and 90b are essentially control ports 68 and 66, respectively, of first generating means 64c and output ports 92d and 92e connected to output legs 72 and 70, respectively. The output port 90e of amplifier 90 is geometrically biased so that when either no signal is applied to the amplifier 90, or when a signal is applied to input port 90b thereof, a fluidic signal results on leg 72 of the generating means 64c. A first generating means resembling the means illustrated as means 64c in FIG. 3C is a Sensor Trigger (code 192681) developed by Corning Glass Works.

FIG. 1 illustrates one embodiment of a demand gas controller circuit 20. The demand gas controller circuit 20 includes a second generating means 96 and a source means 98.

The second generating means 96 of demand gas controller circuit 20 comprises a first output port 96a vented to atmosphere; a second output port 96b connected via line 100 to the source means 98; a first input port 96c connected to the source 46; and, a second input port 96 connected by a line 102 to the output leg 70 of first generating means 64. Second generating means 96 further comprises a substantially closed-loop fluidic path 104 which has a first end 104a perpendicularly intersecting the input port 96c on one side thereof and a second end 104b perpendicularly intersecting the input port 96c on a second side thereof. The ends 104a and 104b are essentially linear at the point of intersection with input port 96c. The fluidic path 104 has thereon one or more timing means, such as a fluid restrictive device 106 and/or a capacitance device 108. As shown in the embodiment of FIG. 1, the restrictive device 106 is a variable resistor and the capacitance 108 is a variable capacitance, such as an elastomeric balloon. The restrictive device 106 and capacitance 108 may be interchanged with similar restrictive devices or capacitances having different values and capacitances.

Source means 98 of the demand gas controller circuit 20 includes a demand valve 110 connected to a source of respirating gas 112 by a line 114. Intermediate the demand valve 110 and source 112 on line 114 are a regulator 116 and a flowmeter 118. The demand valve 110 is also connected to a fluid conveying means, or line 120, for supplying the respirating gas to the nasal prongs 22. A bypass line 122 with a bypass switch 124 thereon is connected between lines 114 and 120 for selectively short-circuiting the demand valve 110. In the above regard, the demand valve 110 may be of any suitable fabrication, such as a moving part valve or a diaphragm valve. An ALCON Series A Model 7986 valve has been preferred in practice.

Figure 4:
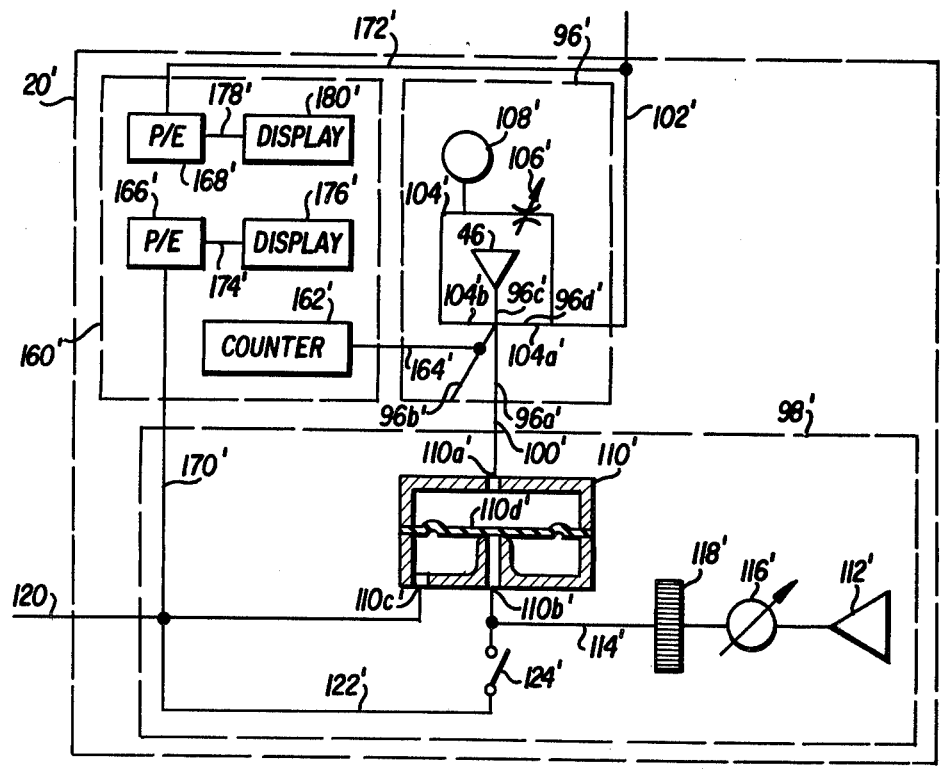
FIG. 4 is a schematic diagram illustrating a demand controller circuit according to an embodiment of the invention; and, FIGS. 5A, 5B, and 5C are graphs illustrating various differing manners of supplying a respirating gas to a patient.

A second embodiment of a suitable demand gas controller circuit is illustrated in FIG. 4. This controller circuit 20' includes a second generating means 96' and a source means 98'. The second generating means 96' comprises a first output port 96a' connected via line 100' to the source means 98'; a second output port 96b' vented to atmosphere; a first input port 96c' connected to the source 46; and, a second input port 96d' connected by a line 102' to the output leg 70 of the first generating means 64. Like the embodiment of FIG. 1, second generating means 96' includes a fluidic path 104 with respective ends 104a' and 104b' and timing means 106' and 108'.

Source means 98' comprises a diaphragm valve 110' connected to a suitable source 112' by a line 114' much in the manner of FIG. 1. Demand valve 110' has a first input port 110a' connected by line 100' to the second generating means 96'; a second input port 110b' connected to the line 114'; an output port 110c' connected to the fluid conveying means 120; and, a flexible diaphragm 110d. In like manner as the FIG. 1 embodiment, the embodiment of FIG. 4 also includes a bypass line 122' having a bypass switch 124' thereon.

In either of the embodiments of FIG. 1 or FIG. 4, the demand gas controller circuit may further comprise a counter and display circuit labeled as 160 in FIG. 1 and 160' in FIG. 4. The circuit 160 of FIG. 1 includes a pneumatic counter 162 connected by a line 164 to line 100. The circuit 160' of FIG. 4 includes a similar pneumatic counter 162' connected by a line 164' to second output port 96b' of second generating means 96'.

At this point, the ensuing discussion of the structure of the FIG. 1 embodiment of the counter and display circuit 160 with its unprimed reference numbers is applicable as well to the embodiment of FIG. 4 with its corresponding but unprimed reference numbers, so that the two figures need not be discussed separately. The circuit 160 further includes two pressure electric devices 166 and 168 suitable for generating an electrical signal having a duration equal to the duration of a fluidic signal applied as an input thereto. Device 166 is pneumatically connected on line 170 to line 120 and device 168 is pneumatically connected on line 172 to line 102. The device 166 is electrically connected by a wire 174 to a display device 176; device 168 is electrically connected by a wire 178 to a display device 180. The display devices 176 and 180 each include unillustrated components such as clocking means, reset means, and a readout means (such as a digital readout).

In either of the embodiments of FIG. 1 or FIG. 4, an oscillator 126 may be connected on line 120 between the patient (nasal prongs 22) and the source means (110 or 110'). The oscillator 126 is employed to create high frequency oscillations in the flow of the respirating gas which increases diffusion of the gas into the lungs. The oscillator 126 may comprise, for example, a rotary motor or a pump. A bypass line 127 with a switch 128 thereon has both its extremities connected to line 120 but on opposing sides of the oscillator 126. Selective activation of the switch 128 effectively short circuits the oscillator 126 and provides for a non-oscillatory flow of respirating gas.

The apneic event circuit 10 is fluidically connected to the output leg 72 of the first generating means 64 and includes an exhaust means 130 (such as a mushroom valve); a variable capacitance device 132 (such as an elastomeric balloon); a digital fluidic device 134 (such as a NOR gate); and, at least one signaling means (such as any of the following: a pneumatically operated digital counter 136a; an alarm 136b; and, an electrocardiogram (ECG) monitor 136c).

The variable capacitance device 132 and NOR gate 134 of the apneic event circuit 10 are connected to the output leg 72 of the first generating means 64 by a line 138. A fluid resistor 140 is interposed on line 138 between the first generating means 64 and the variable capacitance device 132. A fluid path or line 142 is connected in parallel to line 138 around the fluid resistor 140. The mushroom exhaust valve 130 lies on path 142 and is adapted to close when a fluid signal is applied thereon from the direction of generating means 64.

NOR gate 134 comprises a first input port 134a connected to the supply 46; a second input port 134b connected to the line 138; a first output port 134c vented to atmosphere; and, a second output port 134d connected to the signaling means. In this regard, the output port 134d is connected by a line 144 to a pressure electric switch 146 and by lines 144 and 148 to the counter 136a. The pressure electric switch 146 is electrically connected by suitable wires 148 and 150 to the alarm means 136b and the electrocardiogram monitor 136c. The alarm means 136b may be either an audible alarm, a visual alarm, or both.

A pressure/electric device 152 is pneumatically connected by a line 154 to a portion of line 138 which is intermediate the first generating means 64 and the fluid restrictor 140. The pressure electric device 152 is a type which generates an electrical signal having a duration equal to the duration of a fluidic signal applied as an input thereto. The pressure electric device 152 is electrically connected by a wire 156 to a display device 158. The display device 158 is of a type mentioned earlier with reference to devices 176 and 180.

Before discussing the operation of the abovedescribed respirator apparatus, it should be recalled that the applicant has clinically observed in the breathing process that oxygen is absorbed into the blood essentially only during an early stage of inspiration. To illustrate this observation, reference is now made to FIGS. 5A, 5B, and 5C. For purposes of discussion, when a patient breathes at the rate of 10 breaths per minute, each breath averages approximately 6 seconds. To illustrate this example, each of the graphs of FIGS. 5A through 5C have a time axis incremented in seconds (sec) ranging from 0 to 6 seconds. For simplicity, a second axis of the graph is incremented from 0 to 6 liters per minute (L/Min) to indicate the rate of supply of respirating gas to a patient.

Figure 5A:
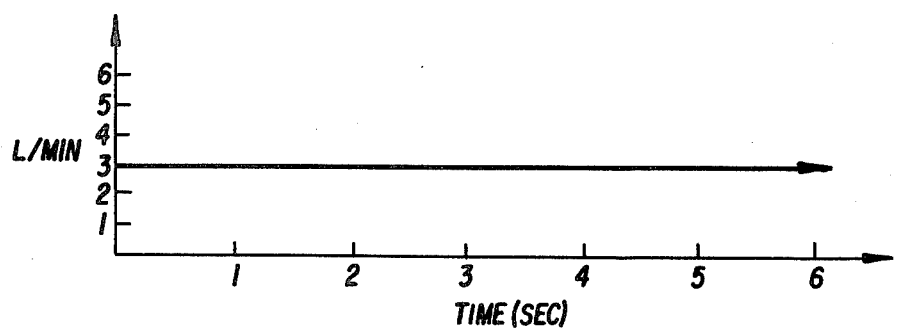

FIG. 5A illustrates a device which continuously supplies respirating gas to a patient. The graph of FIG. 5A shows an essentially straight horizontal line, the area under the line basically corresponding to the amount of gas supplied. For the 6 second time period shown, the gas supplied approximates $$0.3 \, L = 3 \frac{L}{MIN} \times \frac{1 \, MIN}{60 \, SEC} \times 6 \, SEC.$$

Inasmuch as only about 2 seconds of a 6 second breath are required for inspiration, a considerable waste occurs in using the continuous supply device of FIG. 5A.

Figure 5B:
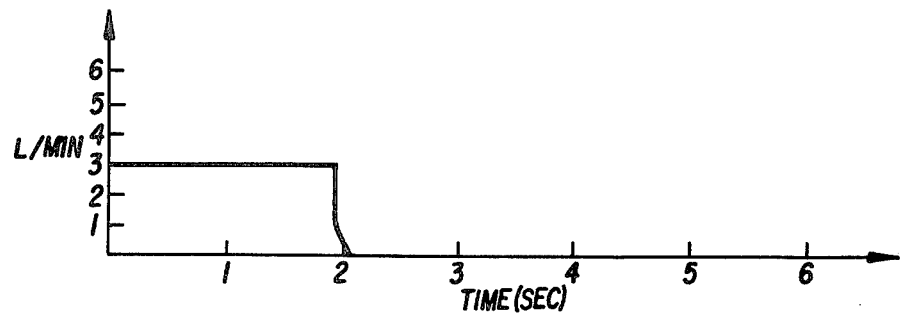

The more economical prior art intermittent demand devices were devised to supply the respirating gas only during inspiration. Such devices are represented by the graph of FIG. 5B, which shows an essentially straight horizontal line lasting for 2 seconds (the approximate length of an entire inspiration). The gas supplied in FIG. 5B approximates 0.1L.

Figure 5C:
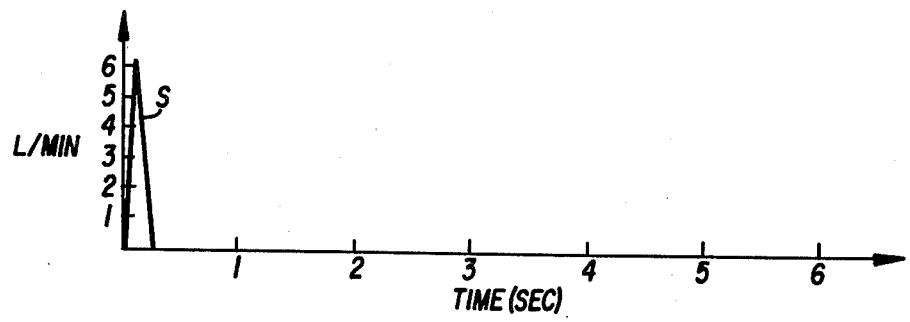

As noted above, the applicant has observed that in operating respirator apparatus it is more advantageous to apply a greater volume of respirating gas per minute at an effective early stage of inspiration rather than a conventional volume per minute rate throughout the duration of inspiration. Hence, FIG. 5C illustrates the applicant's finding that it is preferable to provide the greater volume of oxygen per minute at an early stage of inspiration. This effective early stage is less than approximately one-quarter (and usually approximately one-eighth) of the duration of the inspiration. In particular, FIG. 5C illustrates a "spike" S of oxygen flow of approximately 6 L/Min lasting for approximately 0.25 sec. Hence, the gas supplied in FIG. 5C approximates less than $$0.025 \, L = 6 \frac{L}{MIN} \times \frac{1 \, MIN}{60 \, SEC} \times 0.25 \, SEC.$$

The structure described above and operated in the manner described hereinafter facilitate the supply of a respirating gas, such as oxygen to a patient, in accordance with the manner depicted in FIG. 5C.

When a patient attempts to inhale, a negative pressure created in the nasal prongs 22 and line 24 is sensed by the sensing means 26. As described hereinbefore, the sensing means 26 is capable of detecting a negative pressure as small as 0.5 millimeters of water. Upon sensing a negative pressure created by inspiration, the sensing means 26 generates a fluid signal on output leg 42.

In the above regard, and with reference to the embodiment of the sensing means 26 illustrated in FIG. 2, a negative pressure on sensing line 24 causes the power stream applied at port 34 of the sensing means 26 to deflect to output port 50e. The resultant fluid signal is applied along line 58 to the control port 52a of amplifier 52. As a result, the power stream entering port 52c of amplifier 52 is deflected to output port 52d and creates a signal on line 60. In like manner, the signal on line 60 is applied to control port 54c of an amplifier 54 and results in a fluid signal being created on output leg 42 of the sensing means 26. For the embodiment shown, each stage of amplifiers in the sensing means 26 achieves approximately a 6:1 gain in amplification.

The fluid signal on output leg 42 of sensing means 26 is applied to the control port 68 of first generating means 64 and, as described hereinafter with respect to each alternate embodiment of means 64, ultimately results in a first fluid signal being generated and applied to output leg 70. This first fluid signal has a duration substantially equalling the duration of the patient's inspiration.

In the generating means 64A of the embodiment depicted in FIG. 3A, the signal on output leg 42 is applied to the control port 74a of amplifier 74 and deflects the power stream applied at port 74c to the output port 74d, thereby creating a fluid signal on line 78. The fluid signal on line 78 is applied to the control port 76a of NOR gate 76 and deflects the power stream entering at port 76c to the output 76d, thereby creating the first fluid signal on output leg 70.

In the generating means 64B of the embodiment depicted in FIG. 3B, the signal on output leg 42 is applied to the control port 79a of amplifier 79 for deflecting the power stream entering at input port 79c to the output port 79d, thereby creating a fluid signal on line 83. The fluid signal on line 83 is applied to the flip-flop 80 and particularly to the amplifier 81 at control port 81b. The fluid signal on line 83 deflects the power stream entering port 81c toward output port 81e, thereby creating a fluid signal both on line 86 and feedback line 87a. The signal on line 86 is applied to control port 82a of amplifier 82 for deflecting the power stream entering port 82c toward the output port 82e, thereby generating the first fluid signal on output leg 70.

In the generating means 64C of the embodiment depicted in FIG. 3C, the signal on output leg 42 applied to control port 90a of amplifier 90 overcomes the geometrical bias and deflect the power stream entering port 90c to the output port 90d, thereby creating a fluid signal on line 93. The signal on line 93 is applied to control port 92b of bistable flip-flop 92 and, in a similar manner, deflects the power stream entering at port 92c to the output port 92b, thereby generating the first fluid signal on output leg 70.

The discussion of the operation of the inspiration phase of the respirator apparatus is now bifurcated to take into consideration the two differing embodiments of the demand gas controller circuits 20 and 20' of FIG. 1 and FIG. 4, respectively.

With reference to the demand gas controller circuit 20 of FIG. 1, the first fluid signal generated by means 64 on output leg 70 is applied to the second generating means 96 on line 102. It should be evident from FIG. 1 that, absent a fluid signal on line 102, the power stream entering at port 96c of the generating means 96 is vented to atmosphere through output port 96a. However, when the first fluid signal is applied on line 102 to the second generating means 96, the power stream entering at port 96c is deflected to the output port 96b for a period of time in the manner hereinafter described.

Upon application of the first fluid signal on line 102 to the port 96d of second generating means 96, the power stream entering port 96c is deflected from the output port 96a to the output port 96b, thereby creating a second fluid signal on line 100 which is applied to the source means 98. The first fluid signal on line 102 is also applied to the fluidic path 104 which has thereon timing means (such as the resistance 106 and the capacitance device 108). The timing means delays the passage of the first fluid signal around the closed loop fluidic path 104 for a pre-determined time. That is, an appropriate value is chosen for the resistance of the variable resistor 106 and a capacitance device 108 of appropriate maximum capacity is chosen so that the first fluid signal travelling around the closed loop fluidic circuit 104 will be delayed for a pre-determined time before the signal reaches the second end 104b of the fluidic circuit 104. When the first fluid signal travelling around the closed loop fluidic path 104 reaches the second end 104b, the fluidic pressure on each side of the power stream entering at port 96c is equalized so that the power stream is no longer deflected out the port 96b but instead is again vented to atmosphere through the port 96a.

Thus, the second generating means 96 generates a second fluid signal on line 100, the second fluid signal having a duration related to the duration of the first fluid signal applied from output leg 70 on line 102. The duration of the first fluid signal on line 102 and the second fluid signal on line 100 are in a pre-determined relationship which is dependent upon the values and sizes chosen for the timing means comprising second generating means 96. Such values and sizes should be chosen for this embodiment such that the ratio of the duration of said second fluid signal to the duration of said first fluid signal, and hence the duration of the inspiration, is less than 0.25. In many cases the ratio may approximate 0.125, if desired.

The valve means 110 of source means 98 receives a supply of respirating gas from the source 112 along line 114. Valve means 110 provides the gas to the patient on line 120 for a time period corresponding to the duration of the second fluid signal as received on line 100. Hence, according to the pre-determined relationships given above, the source means 98 supplies respiration gas to the patient for less than 0.5 seconds after the first instance of inspiration.

With reference to the demand gas controller 20' of the embodiment of FIG. 4, the first fluid signal on output leg 70 of generating means 64 is applied on line 102' to the second generating means 96' much in the manner as with the embodiment of FIG. 1. However, it should be noted that absent such a signal the power stream entering at port 96c' is not vented to atmosphere but travels to the output port 96a' as a second fluid signal on line 100'. Upon application of the first fluid signal on line 102' to input port 96d' of the second generating means 96', the power stream entering port 96c' is deflected from the output port 96a' to the output port 96b' where it is vented to atmosphere for a time substantially equivalent to the time required for the first fluid signal to travel around the closed-loop fluidic path 104' and thereafter equalize fluid pressure on both sides of the power stream.

In the above respect, the fluid path 104' resembles the fluid path 104 of the FIG. 1 embodiment and includes similar timing means such as resistor 106' and capacitance 108'. In the embodiment of FIG. 4, the values and sizes of the timing means are chosen such that the ratio of the duration of the second fluid signal applied on line 100' to the duration of the first fluid signal received on line 102' is greater than 0.75 and, in some cases, is greater than 0.875. Of course, the second fluid signal is applied on line 100' only during the latter part of inspiration so that the power stream entering port 96c' is vented to atmosphere through port 96b' substantially at the first instance of inspiration and for a short time period thereafter.

The valve means 110' of source means 98' receives a supply of respirating gas on line 114' from a source 112' and, in the absence of the second fluid signal on line 100', supplies the respirating gas to the the patient on line 120. In this regard, while the presence of the second fluid signal on line 100' biases the diaphram 110d' against the respirating gas input port 110b', the absence of the second fluid signal on line 100' allows the pressure created on line 114' at input port 110b to deflect the diaphragm 110d' and allow passage of the respirating gas through the valve means 110' and out the output port 110c'. Hence, in accordance with the predetermined timing relationship discussed above for the embodiment of FIG. 4, the valve means 110' supplies respirating gas to the patient after a first instance of inspiration for less than 0.5 seconds.

The counter and display circuits 160 and 160' of the respective embodiments provide the operator or attending physician with data relative to the patient's respiratory activity and the operation of the demand gas controller. The counter 162 of FIG. 1 connected to line 100 is incremented whenever a fluid signal is applied to line 100. Thus, counter 162 tabulates the number of inspirations attempted by a patient. The counter 162' of FIG. 4 is connected to second output port 96b' of second generating means 96' and likewise is incremented whenever an inspiration is attempted (whenever the output of means 96' is vented to atmosphere).

Discussing now the further operation of both embodiments of the counter and display circuits 160 and 160' with regard only to the unprimed reference numbers for sake of brevity, the operator or attending physician is able to observe on display devices 176 and 180, respectively, the duration of the supply of respirating gas to the patient on line 120 and the duration of the patient's inspiration as indicated by the fluid signal on line 102. In this regard, the fluid signals are converted to electrical signals by devices 166 and 168, respectively. The duration of the electrical signals are clocked (or timed) by the devices 176 and 180. The devices 176 and 180 display on readout means a numerical value (preferably digital) corresponding to the duration and are then reset in a conventional manner. The display devices 176 and 180 are especially useful as the operator or attending physician adjusts, calibrates, or selectively interchanges the timing means, such as variable resistor 106 and/or capacitor 108, of second generating means 96.

With reference now to both demand gas controller means 20 and 20' of the embodiments of FIG. 1 and FIG. 4, respectively, it should be understood that both illustrated controllers can be easily adapted to supply respirating gas throughout the duration of inspiration if so desired. This can be accomplished in several ways. For example, the value of restrictive device 106 may be chosen so that the resistance is so great on the path 104 that output occurs at output port 96b throughout inspiration. Or, as another example, a bypass line (unillustrated) with a switch thereon may selectively short circuit the second generating means 96. In such a mode of operation, the pre-determined relationship between the first and second fluid signals would be a ratio of 1:1, of a fraction of 1/1.

Again with reference to both demand gas controller means 20 and 20' of the embodiments of FIG. 1 and FIG. 4, respectively, the respirator apparatus can be operated in a continuous mode by closing appropriate bypass switches (124 in FIG. 1 and 124' in FIG. 4). Closing the switch 124 (or 124') allows for the continuous flow of the respirating gas from the source 112 (or 112') through the lines 114, 122, and 120 (or 114', 122', and 120).

With further reference to both embodiments of the demand gas controllers shown in FIGS. 1 and 4, the flowmeter 118 (or 118' in FIG. 4) should be connected intermediate valve means 110 (or 110') and source 112 (or 112') instead of intermediate the valve means 110 (or 110') and the nasal prongs 22. Otherwise, the "spike" S illustrated in FIG. 5C would be dampened, resulting in an insufficient gas supply.

Since during inspiration the generating means 64 applies the first fluid signal on output leg 70 instead of output leg 72, the apneic event circuit 10 does not receive a fluid signal. In fact, during inspiration fluid collected in the variable capacitance device 132 is rapidly discharged out of the mushroom exhalation valve 130 since the valve is not biased shut by a fluid signal applied on fluid path 142. The variable capacitance and elastomeric nature of the device 132, operating in conjunction with the mushroom exhaust valve 130, facilitate the quick discharge of fluid from the variable capacitance device 132. A fixed volume capacitance could not adequately perform this function and would be incompatible with the low pressures used in the fluidic logic circuit discussed herein.

When a patient exhales, a positive pressure is created in the nasal prongs 22 and on the sensing line 24. The sensing means 26 senses the positive pressure and creates a fluid signal on its output leg 40. With reference to the embodiment of the sensing means 26 shown in FIG. 2, the application of positive pressure at control port 50a of amplifier 50 in means 26 causes the power stream entering at port 50e thereof to deflect to output port 50d, thereby creating a signal on line 56. The signal on line 56 is applied to control port 52b of amplifier 52 which, in turn, creates a signal on line 62 for application to control port 54a of amplifier 54. Amplifier 54 then creates a fluid signal on output leg 40. Although not described in detail at this point, it should be understood that the amplifiers 52 and 54 operate in accordance with the same principles as discussed above with regard to the negative pressure operation phase. Of course, fluid signals are applied to opposite input ports and discharged out opposite output ports than those discussed in the negative pressure operation phase.

The fluid signal on line 40 is applied to the control port 66 of first generating means 64 and, in the manner herein described with reference to each of the differing embodiments of FIGS. 3A, 3B, and 3C, generates a first fluid signal on output leg 72 thereof.

In the generating means 64A of the embodiment illustrated in FIG. 3A, the fluid signal on output leg 40 is applied to control port 74b and causes the power stream entering control port 74c to be vented to atmosphere through output port 74e. Therefore, no fluid signal is transmitted on line 78 for application to NOR gate 76. The power stream entering port 76c of the NOR gate 76 continues undeflected and is discharged out the output leg 72.

In the generating means 64B of the embodiment illustrated in FIG. 3B, the signal on output leg 40 is applied to control ports 79b of amplifier 79 and deflects the power stream entering port 79c so that a signal is created on line 84. The signal on line 84 is applied to the flip-flop 80 which ultimately generates a first fluid signal on output leg 72 thereof. Although not described in detail at this point, it should again be understood that the amplifies 81 and 82 comprising flip-flop 80 function in accordance with the same principles discussed above with reference to the negative pressure operating mode. Of course, signals to amplifiers 81 and 82 may be applied at opposing input ports than discussed above and output signals discharged from opposing output ports.

In the generating means 64C of the embodiment illustrated in FIG. 3C, the fluid signal on output leg 40 is applied to control port 90b of amplifier 90 for deflecting the power stream entering port 90c to output port 90e, thereby creating a signal on line 94. The signal 94 entering control port 92a of the bi-stable flip-flop 92 causes the power stream entering port 92c to deflect toward output port 92d, thereby generating a first fluid signal on output leg 72.

In contrasting the three embodiments of the first generating means 64 discussed above, it should be noted that the generating means 64B of FIG. 3B requires an expiration for its output to switch from leg 70 to leg 72. The generating means 64A and 64C, on the other hand, automatically switch their outputs from leg 70 to leg 72 upon the cessation of an inspiration.

Since in the positive pressure operating mode the first generating means 64 generates a first fluid signal on output leg 72, no fluid signal is applied on output leg 70 to the demand gas controller circuit. As discussed separately above with reference to the respective embodiments of demand gas controllers illustrated in FIGS. 1 and 4, the absence of a fluid signal on output leg 70 of the generating means 64 results in supression of the source means 98. Thus, no respirating gas is applied to the patient during expiration.

When generating means 64 generates the first fluid signal on output leg 72 responsive to a sensed positive pressure, the fluid signal is applied to the apneic event circuit 10 by line 138. The signal travels along line 138 until it encounters the fluid resistor 140. Resistor 140 blocks the path of the fluid signal applied on line 138 and causes the fluid signal to travel around the fluid path 142. The fluid signal travelling around the path 142 closes the mushroom exhalation valve 130 which permits the fluid signal to travel further along to the line 138 and into the variable capacitance device 132. The fluid signal is continuously applied to the variable capacitance device 132 so long as the generating means 64 is generating the fluid signal.

In normal breathing the generating means 64 will cease generating the fluid signal on output leg 72 long before the variable capacitance device 132 is filled to its maximum capacity. In this regard, it is recalled that the generating means 64 will no longer discharge a fluid signal on output leg 72 when an inspiration is sensed by the sensing means 26. In this case, the patient is breathing satisfactorily and there is no apneic effect.

In abnormal breathing, however, when the patient fails to inspire the generating means 64 continues to generate a fluid signal on output leg 72. Accordingly, the variable capacitance device 132 continues to expand until it is inflated to its maximum capacity. When the variable capacitance device 132 is inflated to a pressure which expands it to its maximum capacity, the fluid pressure builds on line 138 and causes the power stream entering port 134a of NOR gate 134 to switch from output port 134c to output port 134d. In this manner, the NOR gate 134 creates a fluid signal on line 144 which is used to activate either singularly or in combination various signaling means. As shown in FIG. 1, the fluid signal on line 144 is applied via an intermediate line 148 to a pneumatically operated digital counter 136a which is incremented whenever the NOR gate 134 switches. Line 144 is also connected to a pressure/electric switch 146 which converts the fluid signal on line 144 to an electric signal on lines 148 and 150. The electric signal on line 148 activates an electrocardiogram (ECG) monitor 136c and the electric signal on lines 148 and 150 activates an alarm 136b. As mentioned previously, the alarm may be either visual, audible or both.

Various sizes and types of elastomeric balloons or other appropriate devices may be chosen for the variable capacitance device 132. Factors to be considered in making the choice of which device to use include the elastomeric tension exerted by the device and the maximum fluid-storing capacity of the device. For example, if it were desired that the apneic event circuit 10 indicate that the patient has not inspired within a 20 second interval, the device 132 should be selected so that it can accommodate the volume of fluid generated by generating means 64 for that 20 second period without triggering a switch in NOR gate 134. Of course, should the patient inspire before the variable capacitance device 132 reaches its maximum pressurized capacity, the device 132 acting in conjunction with the mushroom valve 130 is quickly deflated in the manner described above.

The display device 158 of the apneic event circuit 10 enables an operator or attending physician to time the duration of a patient's expiration. The display device 158, together with the pressure/electric device 152, operate in substantially the same manner as similar components in the counter and display circuits 160 discussed above.

While the invention has been particularly shown and described with reference to the preferred embodiments thereof it will be understood by those skilled in the art that various alterations in form in detail may be made therein without departing from the spirit and scope of the invention. For example, the counter 162 may alternatively be connected to lines 120 or 102. Moreover, while the invention has been particularly shown and described with reference to a respirator adapted for clinical use (as with a patient, for example), it should be understood that the invention may be used in other fields. For example, the invention may be used in conjunction with gas supply to or apnea detection in a subject in aeronautical, subteranean or underwater environment.

The embodiments of the invention in which an exclusive property or privilege is claimed are defined as follows:

1. A respirator apparatus comprising:
   means for sensing pressure flow in a respiratory system;
   first generating means fluidically connected to said sensing means for generating a first fluid signal, said generating means further comprising at least a first output port and a second output port, said generating means being adapted to discharge said first fluid signal either out said first output port or said second output port;
   an apneic event fluid circuit, said circuit comprising:
   a variable capacitance device fluidically connected to said first output of said first generating means, said variable capacitance device having a pre-determined maximum capacity for storing a volume of fluid substantially equal to a volume of fluid created by the continuous generation and application of said first fluid signal for a predetermined time;
   exhaust means fluidically connected to said variable capacitance device, said exhaust means being adapted to close when said first generating means is generating said first fluid signal at said first output port and to open when said first generating means is not generating said first fluid signal at said first output port; and,
   indicator means responsive to the pressure in said variable capacitance device, said indicator means being adapted for activation when the pressure created in said variable capacitance device by the continuous application of said first fluid signal for a time greater than the pre-determined time period exceeds the maximum capacity of the variable capacitance device; and,
   a demand gas controller circuit, said circuit comprising:
   source means fluidically connected to said second output port of said first generating means and responsive to said first fluid signal for providing respirating gas to said patient for a time period corresponding to the duration of said first fluid signal; and,
   fluid conveying means for conveying said respirating gas from said source means to said patient.

2. A respirator apparatus comprising:
   means for sensing pressure flow in a respiratory system;
   first generating means fluidically connected to said sensing means for generating a first fluid signal, said generating means further comprising at least a first output port and a second output port, said generating means being adapted to discharge said first fluid signal either out said first output port or said second output port;
   an apneic event fluid circuit, said circuit comprising:
   a variable capacitance device fluidically connected to said first output of said first generating means, said variable capacitance device having a pre-determined maximum capacity for storing a volume of fluid substantially equal to a volume of fluid created by the continuous generation and application of said first fluid signal for a pre-determined time;
   exhaust means fluidically connected to said variable capacitance device, said exhaust means being adapted to close when said first generating means is generating said first fluid signal and to open when said first generating means is not generating said first fluid signal; and,
   indicator means responsive to the pressure in said variable capacitance device, said indicator means being adapted for activation when the pressure created in said variable capacitance device by the continuous application of said first fluid signal for a time greater than the pre-determined time period exceeds the maximum capacity of the variable capacitance device; and,
   a demand gas controller circuit, said circuit comprising:
   second generating means fluidically connected to said second output port of said first generating means for generating a second fluid signal having a duration related to the duration of said first fluid signal by a pre-determined relationship;
   source means fluidically connected to said second generating means and responsive to said second fluid signal for providing respirating gas to said patient for a time period relative to the duration of said second fluid signal; and,
   fluid conveying means for conveying said respirating gas from said source means to said patient.

3. A method of supplying supplemental dosages of respirating gas to a spontaneously breathing in vivo respiratory system having an inspiration period and an expiration period, said inspiration period being of duration $T_2$ during which period a negative pressure relative to ambient pressure exists in said in vivo respiratory system at the location whereat respirating gas is introduced to said system, said expiration period comprising a positive pressure relative to ambient pressure existing in said in vivo respiratory system at the location whereat respirating gas is introduced to said system, said method comprising the steps of:
   (1) sensing initiation of said inspiration period;
   (2) using timing means to predetermine a duration $T_1$ for which a dose of respirating gas is to be supplied to said in vivo respiratory system, said duration $T_1$ being less than the duration $T_2$ of negative pressure relative to ambient pressure occuring in said in vivo respiratory system during said inspiration period; and,
   (3) supplying immediately in response to said sensed inspiration a dose of respirating gas to said in vivo respiratory system, said dose being supplied only for the duration $T_1$, said dose being supplied substantially at the beginning of said sensed inspiration, said dose of gas being supplied at a rate $R_1$, said rate $R_1$ being set at a value such that it produces at least as great a rise in the partial pressure of said gas in blood interfacing with said respiratory system as the continuous application of said gas at a lower rate $R_2$ for the duration $T_2$; and,
   (4) automatically repeating steps (1), (2), and (3) for a plurality of consecutive inspiration periods.

4. The method of claim 3, wherein $T_1$ is less than $0.25 \times T_2$.

5. The method of claim 3, wherein $T_1$ is less than 0.5 second.

6. The method of claim 3, further comprising the step of:
   determining the occurrence of an apneic event when a next expected occurrence of negative pressure created by an attempted inspiration of said in vivo respiratory system is not sensed within a pre-determined time period after a previous occurrence of negative pressure in said in vivo respiratory system.

7. The method of claim 6, wherein $T_1$ is less than $0.25 \times T_2$.

8. The method of claim 6, wherein $T_1$ is less than 0.5 second.

* * * * *